(12) United States Patent
Waggot et al.

(10) Patent No.: US 8,505,387 B2
(45) Date of Patent: Aug. 13, 2013

(54) APPARATUS AND METHOD FOR APPLYING A CYCLICAL LOAD TO AN ELONGATE SPECIMEN

(75) Inventors: Alan Waggot, Crawcrook (GB); Peter Hope, Consett (GB); Ian Williamson, Prudhoe (GB); Richard Court, Consett (GB)

(73) Assignee: National Renewable Energy Centre Limited, Blythe (GB)

( * ) Notice: Subject to any disclaimer, the term of this patent is extended or adjusted under 35 U.S.C. 154(b) by 282 days.

(21) Appl. No.: 12/937,425

(22) PCT Filed: Mar. 30, 2009

(86) PCT No.: PCT/GB2009/050307
§ 371 (c)(1),
(2), (4) Date: Nov. 19, 2010

(87) PCT Pub. No.: WO2009/127851
PCT Pub. Date: Oct. 22, 2009

(65) Prior Publication Data
US 2011/0056300 A1 Mar. 10, 2011

(30) Foreign Application Priority Data

Apr. 14, 2008 (GB) .................................. 0806681.3

(51) Int. Cl.
*G01N 3/32* (2006.01)
(52) U.S. Cl.
USPC .............................................. 73/808; 73/760
(58) Field of Classification Search
USPC ..................................... 73/760, 799, 808, 809
See application file for complete search history.

(56) References Cited

U.S. PATENT DOCUMENTS

| 2,425,273 | A | | 8/1947 | Watter | |
|---|---|---|---|---|---|
| 4,003,246 | A | * | 1/1977 | Cain | 73/799 |
| 4,248,096 | A | * | 2/1981 | Marcum | 73/828 |
| 4,501,139 | A | * | 2/1985 | Petersen | 73/117.01 |
| 7,953,561 | B2 | * | 5/2011 | Musial et al. | 702/42 |
| 2006/0037402 | A1 | | 2/2006 | Musial et al. | |

FOREIGN PATENT DOCUMENTS

| DE | 102005038033 A1 | 2/2007 |
|---|---|---|
| JP | 04164231 A | 6/1992 |
| WO | WO-/2004/005879 A1 | 1/2004 |

OTHER PUBLICATIONS

Ruchaud, Nicolas, "International Search Report", for PCT/GB2009/050307 as mailed Jul. 1, 2009, 5 pages.

* cited by examiner

*Primary Examiner* — Max Noori
(74) *Attorney, Agent, or Firm* — Winstead PC

(57) ABSTRACT

An apparatus for applying at least one cyclical load to an elongate specimen, comprising at least two reciprocating mass means (1) each comprising a mass (6) and an actuator (16), wherein the actuator (16) is (5) operatively associated with the mass (6) to move the mass (6) along a linear displacement path, mounting means (2) for mounting each actuator (16) to a specimen, and a control system operatively associated with each actuator (16), the control system operating each actuator (16) to reciprocate its corresponding mass (6) along its respective linear displacement path, wherein the reciprocating mass means (1) are spaced apart such that the actuators (16) move their corresponding masses (6) on separate, and substantially parallel, linear displacement paths is disclosed.

26 Claims, 3 Drawing Sheets

APPARATUS AND METHOD FOR APPLYING A CYCLICAL LOAD TO AN ELONGATE SPECIMEN

Figure 1:
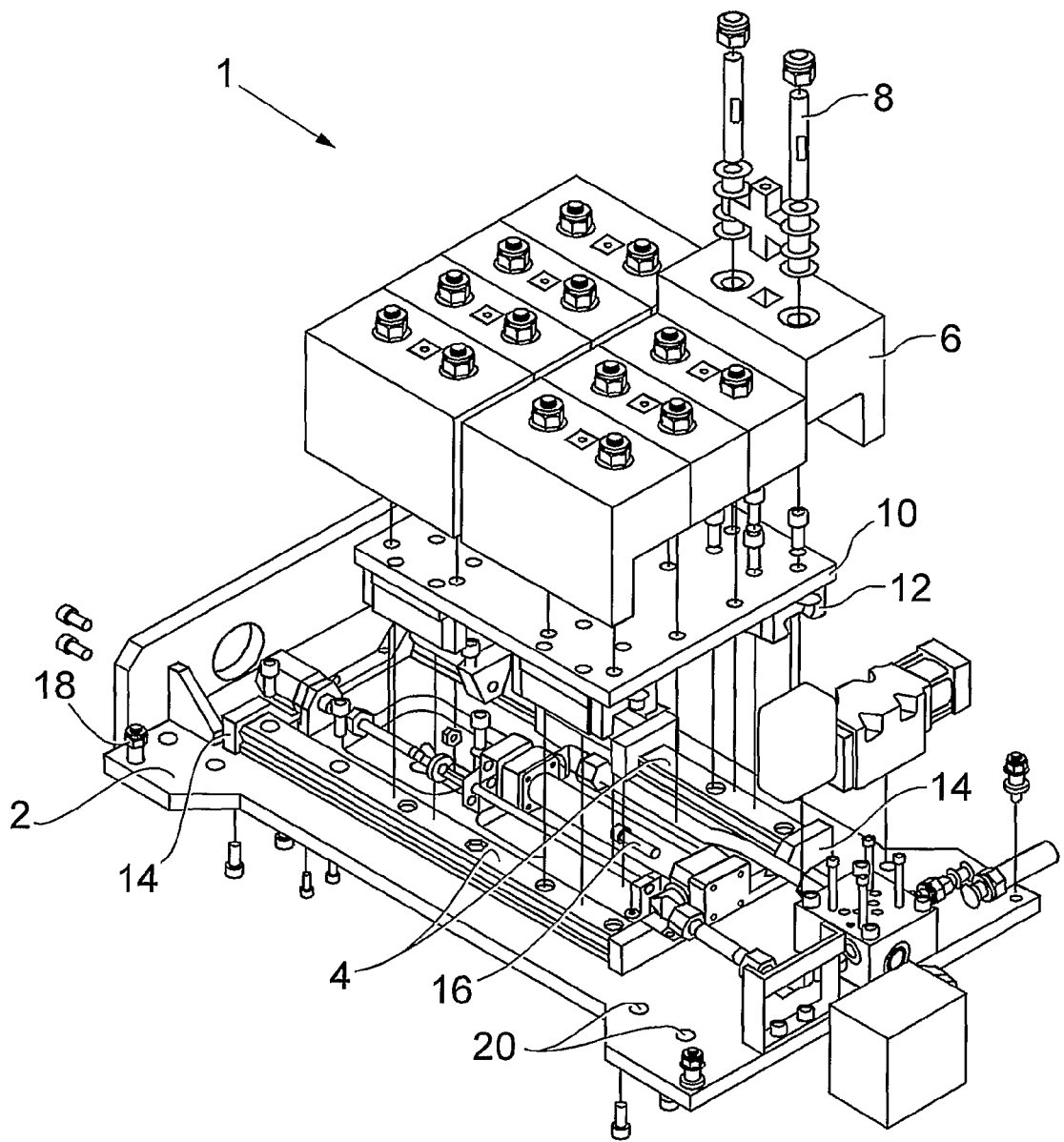

The present invention relates to systems for applying structural loads to specimens and more specifically for applying cyclic structural loads to an elongate structure such as a wind turbine blade to cause the structure to vibrate, especially at a resonance frequency.

The rotor of a typical wind turbine comprises a plurality of long, slender turbine blades mounted to and extending from a hub. The rotor is coupled to one or more electrical generators which generate electricity when actuated by the rotating motion of the hub. To increase the efficiency of the wind turbine, longer and larger blades are being produced to capture an increased amount of energy from a prevailing wind. The increase in blade size results in an increase in static and dynamic loads being subjected thereon. Therefore, it is extremely desirable to test the blades before assembly and installation to ensure they do not fail whilst in service.

Typically, in order to test a wind turbine blade, it is horizontally orientated on its side and constrained in all directions at its root by bolting the same to a suitable test bed. Loads are then applied to the blade at suitable locations and in various directions. For example, one type of load is applied vertically downwards and perpendicularly to a longitudinal axis of the blade; often referred to as a bending or flap load. Another type of load is also applied perpendicularly to the longitudinal axis of the blade, but also perpendicular to the direction of the flap load. This type of load is often referred to as a lateral or edge load. These tests may be either static or dynamic for determining the stiffness or strength of a blade or its fatigue performance, respectively.

Another type of test is to cause the blade to resonate at its different modes of resonance. To cause the blade to resonate, it is known to apply a cyclic bending load to vibrate the blade at a desired location, typically near the blade tip, to cause the blade to resonate in the longitudinal direction. The blade generally begins to resonate in its first mode and then subsequent modes as the frequency of the cyclic bending load is increased. The resonant vibration of the blade reduces the amount of energy otherwise required to apply bending or lateral loads, for example. Therefore, causing the blade to resonate is desirable, particularly for testing larger blades.

However, known systems for testing wind turbine blades are unable to fully simulate real-life conditions. For example, each blade is subjected to both bending and lateral loads during service by the forces of a prevailing wind and many known systems are unable to simultaneously apply both these load types to the blade. Usual practice is to perform the bending and lateral resonant tests separately at different times. Between the different tests, the means for applying a cyclic load to the blade must be removed, the bolts or clamps constraining the root of the blade must be loosened, the blade then requires rotating into the desired orientation and the bolts or clamps must be tightened before the different test can be performed. As a result, the time required to perform the separate tests is lengthy and therefore costly.

PCT/US2002/020991 describes a system for testing wind turbine blades comprising a resonant actuator having a reciprocating mass within a cumbersome frame which is mounted on the upper side of a blade horizontally orientated and constrained at its root. The resonant actuator vibrates the blade in a vertical direction causing it to resonate perpendicular to the longitudinal axis. The system comprises an optional transverse load actuator which is floor-mounted and comprises a pushrod pivotally mounted to the edge of the blade. The transverse actuator transmits a force and motion to the blade in a lateral direction. The transverse actuator does not operate in resonant mode. Transverse displacement is effected by the action of the pushrod of a forced hydraulic ram. The pushrod of the transverse actuator is pivotally mounted to the blade to accommodate the vertical displacement of the vibrating blade.

However, both the transverse actuator and resonant actuator are typically large and cumbersome. The resonant actuator includes a large reciprocating mass to cause the blade to vibrate. For large blades, the mass may be as high as a few tonnes to cause the blade to vibrate, and even more in some cases. This is particularly undesirable when setting up the test, for example. The mass generally reciprocates along an axis which is perpendicular to and intersects the longitudinal axis of the blade. Therefore, setting up the test and accurately positioning the resonant actuator on the blade is particularly time consuming and costly. Only bending loads can be applied to the blade with the large mass as mounting such a mass to the edge of a blade for lateral loading is inconveniently difficult, if not impossible. In addition, the resonant actuator must be mounted on the blade in a desired position and suitable mounts must be fabricated which are specific to the desired position along the blade axis. If a different position is desired, new mounts must be fabricated as the blade profile changes along the blade. The resonant actuator including the mass has its own centre of gravity. If the centre of gravity of the resonant actuator is offset from the longitudinal axis of the blade this results in a moment being imposed on the blade when it is moved in a lateral direction by the transverse actuator. This imposes unrealistic loading on the blade and has a detrimental affect to the behaviour of the blade being tested. A result of this is incorrect or unrealistic test results.

The transverse actuator is hydraulically forced and complexly mounted to the blade and the blade requires a degree of modification to accommodate this attachment. This is particularly undesirable where a customer requires the blade to be returned after testing. Although the transverse actuator is pivotally attached to the blade, the behaviour of the blade is affected by the attachment of the transverse actuator to the blade and the coupling of the blade to the floor via this pivotal attachment. In particular, the pushrod of the transverse actuator follows an arc as it moves laterally and the blade vibrates vertically causing unrealistic loads to be imposed to the blade. The system therefore attempts to simultaneously apply both bending and lateral cyclic loads to the blade but the testing conditions are not representative of the conditions experienced by the blade in the field.

Therefore, a system for testing wind turbine blades which is capable of simultaneously applying bending and lateral cyclic loads to a blade in a controlled and practical manner in order to simulate real-life conditions is required.

A first aspect of the present invention provides an apparatus for applying at least one cyclical load to an elongate specimen, comprising:
  at least two reciprocating mass means each comprising a mass and an actuator, wherein the actuator is operatively associated with the mass to move the mass along a linear displacement path;
  mounting means for mounting each actuator to a specimen; and
  a control system operatively associated with each actuator, the control system operating each actuator to reciprocate its corresponding mass along its respective linear displacement path;

wherein the reciprocating mass means are spaced apart such that the actuators move their corresponding masses on separate, and substantially parallel, linear displacement paths.

Suitably, the reciprocating mass means are adapted to be separately mounted in spaced manner in a direction transverse to a longitudinal midline or longitudinal axis of the specimen. In particular the reciprocating mass means are adapted to be mounted and spaced so as to allow the load applied either side of the longitudinal axis of the specimen to be balanced in use.

It will be understood by a person skilled in the art that term 'longitudinal axis' is generally known to be a longitudinal midline running along the length of a specimen and is not limited to an axis of rotation or symmetry.

Mounting the at least two reciprocating mass means in spaced manner so that a load is applied on either side of the longitudinal axis of the specimen advantageously enables provision of a more readily balanced test configuration compared with a single load being mounted on a specimen as in known systems. As described above, a single mass mounted off the longitudinal axis of the specimen unbalances the test configuration and applies unrealistic moments to the specimen during testing, particularly if a lateral load is simultaneously applied. Careful centralisation of a single mass to avoid load imbalance is a significant practical issue in such systems.

Spacing the at least two reciprocating mass means allow the mass required to cause the specimen to vibrate, and preferably resonate, to be effectively split into the corresponding masses of the at least two reciprocating mass means. The corresponding masses of each reciprocating mass means move along parallel transversely spread displacement paths which may then be disposed on either side of the specimen and perpendicular to its longitudinal axis. Splitting the reciprocating mass means makes a more balanced cyclic loading of the specimen in a direction perpendicular to the longitudinal axis easier to achieve. Setting up the test configuration and, in particular, mounting each reciprocating mass means to the specimen is made easier due to the ability to 'split' masses either side of the longitudinal axis.

To give effect to this, the at least two reciprocating mass means are laterally spaced to allow the defining of a force balance point about which applied forces can be balanced, so that any turning moment about the force balance point is reduced and preferably minimised as the masses are caused to reciprocate. For example, the at least two reciprocating mass means comprise paired groups of reciprocating mass means spaced either side of a force balance point so that applied forces can be balanced about the force balance point. Preferably the at least two reciprocating mass means comprise exactly one split pair of reciprocating mass means, split across such a force balance point in such manner that applied forces can be balanced about the force balance point. In particular no undesirable torque loading is introduced.

Advantageously, the improved load balance tolerance conferred by split masses over a single mass produces a system which will tolerate movement of the masses a greater distance along their associated displacement paths without applying additional moments to the specimen. This can allow total mass to be reduced for a given load.

Preferably, the control system is adapted to move the corresponding masses of the at least two reciprocating mass means along their parallel displacement paths in phase with each other. Alternatively, the corresponding masses of the at least two reciprocating mass means may be controlled to move out of phase with each other to apply a torsional load to the specimen about a longitudinal axis, if desired.

Preferably, the at least two reciprocating mass means are arranged to move their corresponding masses along parallel linear displacement paths in a first general direction and at least one further reciprocating means is arranged to simultaneously apply a cyclical load in a second direction substantially perpendicular to the first direction. The at least one further reciprocating means simultaneously applies a second cyclic load to the specimen in a direction which is substantially perpendicular to the first direction of the cyclical load applied by the at least two reciprocating mass means.

Suitably, the specimen may have an aerofoil cross section having wide upper and lower surfaces and narrow edges, for example being a wind turbine blade in a horizontally orientated test position. Suitably, the at least two reciprocating mass means may be provided with mounting means for mounting on opposing upper and lower surfaces of the specimen and the at least one further reciprocating means may be provided with mounting means for mounting on an edge, or vice versa.

Suitably, the at least two reciprocating mass means may apply a cyclic bending load to the specimen and the further reciprocating means may simultaneously apply a cyclical lateral load to the specimen. Thus, the at least two reciprocating mass means may constitute in this mode of operation a resonant actuator and further reciprocating means may constitute a transverse actuator in familiar manner.

Advantageously, the at least one further reciprocating means is in no way coupled with the ground and operates independently of the at least two reciprocating mass means. This ensures the simultaneous loading applied to the specimen is more realistic than the loading applied by known systems in the art.

The further reciprocating means may suitably comprise at least one secondary reciprocating mass means having a mass and operatively associated actuator in similar manner to the at least two primary reciprocating mass means hereinabove described. Preferably, the further reciprocating means comprises a plurality of transversely spaced secondary reciprocating mass means each having a mass and operatively associated actuator. Preferably, the further reciprocating means comprises paired groups of secondary reciprocating mass means each having a mass and operatively associated actuator spaced either side of a force balance point so that applied forces can be balanced about the force balance point. Conveniently, the further reciprocating means comprises exactly one split pair of secondary reciprocating mass means, split across such a force balance point so that applied forces can be balanced about the force balance point.

Preferably, the apparatus comprises a primary reciprocating means comprising a primary pair of reciprocating mass means, as above described, and at least one further reciprocating means comprises a secondary pair of reciprocating mass means. Providing a secondary pair of reciprocating mass means ensures the different loads applied by the primary and secondary pairs of reciprocating mass means are balanced and the overall test configuration has minimal effects on the vibrational behaviour of the specimen, particularly at its modes of resonance frequency.

Preferably, the first direction is along a vertical displacement path and the second direction is along a horizontal displacement path. Suitably, the primary pair of reciprocating mass means apply a cyclic bending load to the specimen and the secondary pair of reciprocating mass means simultaneously apply a cyclic lateral load to the specimen.

Preferably, each actuator is mounted at a first end to a base of the mounting means and at a second end to its corresponding mass. The base is suitably adapted to mount the actuator to the specimen and so the first end of the actuator is fixed relative to the second end attached to the mass being free to move along the associated linear displacement path. Suitably, the actuator may be a linear actuator. A linear hydraulic actuator may be used. Alternatively, other suitable means may be used, such as a linear electric actuator or solenoid.

Preferably, each mass is slideably mounted relative to the base of its associated reciprocating mass means.

Preferably, each mass is slideably coupled to at least one linear bearing.

Preferably, each mass is removeably mounted on a carriage plate being slideably coupled to the at least one linear bearing. Suitably, the linear bearing may be a rail to which the carriage plate is adapted to couple with. The rail slideably mounts and guides the carriage plate and the mass thereon along its associated linear displacement path. Of course, other suitable means may be used to slideably mount each mass on its associated reciprocating mass means and guide it along its linear displacement path.

The control system is configured to allow the displacement of each mass along its associated linear displacement path to be varied in order to control the cyclic loading applied to the specimen. While the apparatus may be operated in an 'open-loop' mode (i.e. without feedback) to achieve this function, it is preferred to provide the apparatus with a feedback loop to allow the apparatus to be operated in a 'closed-loop' mode. Preferably, the apparatus further comprises a feedback sensor operatively associated with the control system, the feedback sensor producing a feedback signal, the control system being responsive to the feedback signal thereby to operate each actuator in response to the feedback signal to change a displacement of each mass along its associated linear displacement path. The control system receives a feedback signal from a feedback sensor and changes the displacement of the mass of a reciprocating mass means in accordance with the feedback signal sensed.

Preferably, the feedback sensor comprises one or more of a strain gauge, an accelerometer or a displacement sensor. Suitably, the feedback sensor may sense other parameters and behaviour characteristics of the specimen, such as modal frequency or stress, for example.

Preferably, the displacement sensor comprises a datum located on the specimen and a datum tracking device remotely positioned from the specimen which tracks a position of the datum. A datum is mounted on, or otherwise defined on the surface of, the specimen and a remotely positioned datum tracking device tracks a position of the datum. Suitably, the datum may comprise a point, line, edge or plane on the specimen or may comprise a sticker or mark applied to the specimen. Alternatively, the datum may comprise a laser. Suitably, the datum tracking device may comprise a camera, for example.

Such a datum tracking approach represents a novel and effective approach to retrieve position information for a loaded specimen dynamically during a test.

Preferably, the mounting means comprises an adjustable clamp for clamping to an outer surface of a specimen at any position along the specimen. Suitably, the clamp is adapted to fit between an outer surface of the specimen and at least one reciprocating mass means to mount the same to the specimen. Advantageously, the clamp is adjustable to allow the reciprocating mass means to be mounted at any position along the specimen. This is particularly convenient where the profile of the specimen, e.g. a wind turbine blade, is strictly confidential and a customer for whom the specimen is to be tested is reluctant to disclose the specimen profile before testing commences. With known systems, the profile must be supplied to the tester before testing commences to allow time for custom mounting brackets, for example, to be fabricated for the specific mounting position on the specimen. Where the profile of the specimen changes along its longitudinal axis and a different position for mounting the reciprocating mass means is desired, e.g. a different loading point for a separate test, new mounting means must be fabricated specifically for the new position. By using an adjustable clamp, the profile of the specimen at a desired location along the specimen is not required before testing as the clamp can simply be adjusted during setup of the apparatus before testing commences. Eliminating the need for custom-made mounting means reduces the time and cost required to set up the test.

Preferably, the clamp comprises a platform adapted to attach to the base of the mounting means. Preferably, the platform comprises a plurality of holes each being adapted to slideably receive a complementarily-shaped pin having a first end and a second end, wherein the first end of each pin interfaces with an outer surface of the specimen. Suitably, the first end of each pin comprises a resilient portion to protect the outer surface of the specimen when the clamp is in situ. The resilient portion may be a cap placed over the first end and may be a rubber material, for example.

Preferably, the second end of each pin comprises a stop to limit the slideable movement of the pin in the corresponding hole. Suitably, the stop may be an outwardly extending shoulder, similar to a bolt head, to limit the slideable movement of each pin in its corresponding hole.

In a possible embodiment, the pins and holes are threaded. To adjust the clamp to fit a desired profile of the specimen, each pin is adjusted by twisting it in either the clockwise or anticlockwise direction to lower or raise the pin in its corresponding hole, respectively. After adjustment, each pin is constrained in its longitudinal direction by the screw threads.

Other suitable means of adjusting and constraining the pins may be used, such as an interference fit of each pin within its corresponding hole. For example, a pin may be in the form of a wooden dowel which is configured correspondingly to the profile of a hole. Pins are inserted, back ends sawn off, and a plate is mounted behind.

In accordance with the invention in a further aspect a method for vibrating an elongate specimen, comprises the steps of:
providing at least two reciprocating mass means each comprising a mass and an actuator operatively associated with its corresponding mass to move its mass along a linear displacement path;
mounting each reciprocating mass means in spaced relationship on the specimen; and
providing a control system operatively associated with each actuator to operate each actuator to reciprocate the corresponding masses of each reciprocating mass means along separate, and substantially parallel, linear displacement paths.

Preferably the reciprocating mass means are mounted and spaced so as to allow the load applied either side of a force balance point, preferably corresponding generally to a longitudinal axis of the specimen as hereinbefore defined, to be balanced in use.

Mounting the masses in spaced manner so that a load is applied on either side of the longitudinal axis of the specimen balances the configuration and reduces twisting loads, particularly if a lateral load is simultaneously applied.

Preferably, the method comprises applying a cyclical load in such manner and at such frequency that a specimen is caused to vibrate in a characteristic resonance mode.

Preferably, a specimen is elongate, and is restrained at a first end and free at a second end, and the method comprises mounting the reciprocating mass means between the first end and the second end and reciprocating the masses to apply a bending load in a direction perpendicular to an elongate direction of the specimen.

Preferably, the method comprises the steps of:
arranging the at least two reciprocating mass means to move their corresponding masses along parallel linear displacement paths in a first direction;
providing at least one further reciprocating means; and
arranging the at least one further reciprocating means to simultaneously apply a cyclical load in a second direction substantially perpendicular to the first direction.

Preferably, the at least two reciprocating mass means comprise a primary pair of reciprocating mass means and the at least one further reciprocating means comprises a secondary pair of reciprocating mass means.

Preferably, the specimen is elongate and each of the first and second directions is a direction perpendicular to an elongate direction of the specimen.

Preferably, a specimen is elongate and is restrained at a first end and free at a second end so as to define a reference plane, corresponding for example where the specimen is an elongate rotational structure to a plane of rotation in use, and the first direction is a direction perpendicular to the reference plane of the specimen to produce a bending deflection and the second direction is a direction parallel to the reference plane of the specimen to produce a transverse deflection.

Preferably, the first direction is along a vertical displacement path and the second direction is along a horizontal displacement path.

Preferably, the method comprises the further steps of:
detecting one or more of a strain, acceleration or displacement of the specimen; and
controlling a displacement of the masses along its corresponding linear displacement path in accordance with the detection.

Preferably, the method comprises the further steps of:
locating a datum on the specimen;
positioning a camera remotely from the specimen; and
tracking a position of the datum with the camera.

Preferably, the datum comprises a laser.

Preferably, the method comprises the further mounting steps of:
providing an adjustable clamp comprising a platform having a plurality of holes each being adapted to receive a complementarily-shaped pin having a first end and a second end;
adjusting each pin in accordance with a specimen profile so the first end of each pin interfaces with an outer surface of the specimen to mount the platform to the specimen in a desired orientation; and
attaching a reciprocating mass means to the platform.

Figure 2:
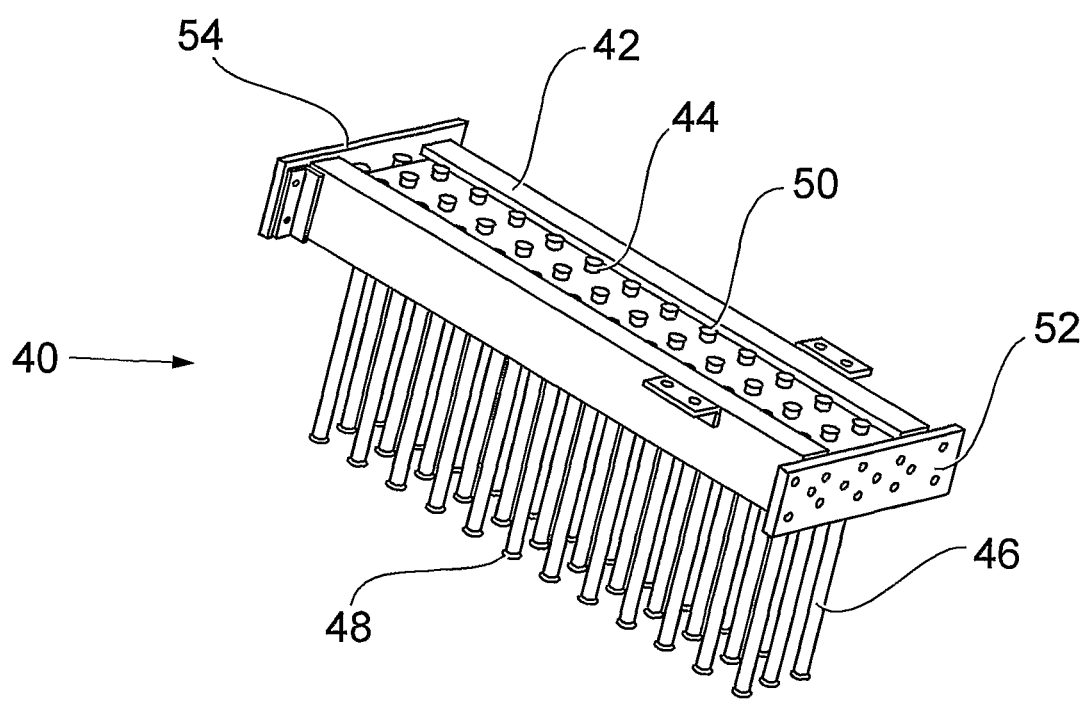
Figure 3:
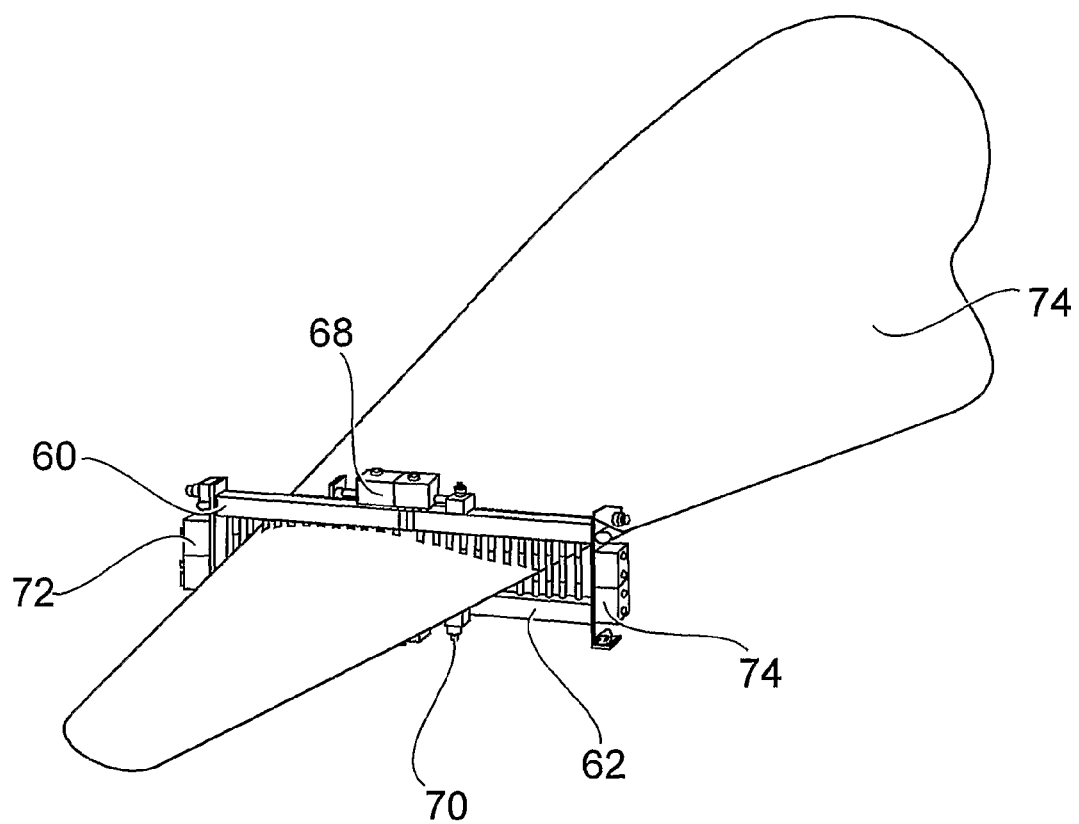

An embodiment of the present invention will now be described, by way of example only, with reference to the accompanying drawings, in which:

FIG. 1 shows a single reciprocating mass means;
FIG. 2 shows an adjustable clamp for mounting a reciprocating mass means to a specimen; and
FIG. 3 shows two separate pairs of reciprocating mass means mounted on a wind turbine blade for simultaneously applying bending and lateral cyclic loads to the blade.

As shown in FIG. 1, a reciprocating mass means 1 includes a base plate 2 for mounting the reciprocating mass means 1 to a specimen, such as a wind turbine blade (not shown). The base plate 2 includes two spaced rails 4 attached thereto, each rail 4 having a first and second flange connected by a web to define an I-section.

The reciprocating mass means 1 further includes a plurality of mass units 6 individually mounted by bolts 8 to a carriage plate 10. The mass units 6 may be a suitable high density material such as lead, for example. The carriage plate 10 has four runners 12 attached to its base. Each runner 12 comprises a channel being complementarily-shaped with the first flange of each rail 4 to allow the carriage plate 10 to slide linearly along the rails 4. The coupled relationship of the runners 12 and the rails 4 also prevents the carriage plate 10 and the mass units 6 coming away from the rails 4. The rails 4 are also provided with stops 14 at their free ends to prevent the runners 12 sliding off the rails 4 in a longitudinal direction. The runners 12 and rails 4 may include friction-reducing means such as a lubricant and/or bearings, for example.

The carriage plate 10 is mechanically coupled to a first end of a linear hydraulic actuator 16. A second end of the actuator 16 is fixed to the base plate 2. The actuator 16 is operatively controlled to move the carriage plate 10 and the mass units 6 mounted thereon along a linear displacement path guided by the rails 4. The linear hydraulic actuator 16 may alternatively by an electric actuator, such as a solenoid. A control system (not shown) operates the actuator 16 to reciprocate the carriage plate 10 and the mass units 6 mounted thereon along the linear displacement path.

Once mounted to an elongate specimen, horizontally orientated and constrained at one end, the reciprocating mass means 1 causes the specimen to vibrate perpendicular to its longitudinal axis. The displacement of the carriage plate 10 and mass units 6 along the linear displacement path can be controlled and varied to cause the specimen to vibrate at different frequencies, such as its resonant frequency. A feedback sensor (not shown) may optionally be operatively associated with the control system, to produce a feedback signal, the control system being responsive to the feedback signal thereby to operate the actuator 16 in response to the feedback signal to change a displacement of the carriage plate 10 and mass units 6 along the linear displacement path.

In accordance with the embodiment of the present invention, at least two reciprocating mass means 1 are spaced apart such that the actuators 16 move their corresponding mass units 6 on separate, and substantially parallel, linear displacement paths. Splitting the reciprocating mass means 1 makes a more balanced cyclic loading of the specimen in any direction perpendicular to the longitudinal axis easier to achieve. Arranging the reciprocating mass means 1 either side of the longitudinal axis of the specimen ensures the centre of gravity of the test configuration is low, significantly reducing undesirable loads during testing. Setting up the test configuration and, in particular, mounting each reciprocating mass means 1 to the specimen is also made easier due to the ability to 'split' masses either side of the longitudinal axis, as described above.

To give effect to this, the at least two reciprocating mass means 1 are spaced to allow the defining of a force balance point about which applied forces can be balanced, so that any turning moment about the force balance point is reduced and preferably minimised as the masses 6 are caused to reciprocate.

Therefore, to apply a balanced cyclic bending load to a specimen, a reciprocating mass means 1 is mounted on either side of the specimen and arranged on the specimen to orientate their associated linear displacement paths in a vertical direction. Their corresponding masses 6 are thereby reciprocated up and down in phase along a vertical displacement path and a cyclic bending load is applied to the specimen. The displacement of each reciprocating mass means can be controlled for a desired specimen frequency. Individual mass units 6 can also easily be added or removed to vary the total mass and applied load in accordance with the size or stiffness of the specimen and also the desired specimen frequency to be achieved.

Alternatively, a pair of reciprocating mass means 1 are mounted on the upper and lower surfaces of the specimen and arranged on the specimen to orientate their associated linear displacement paths in a horizontal, lateral direction being perpendicular to the longitudinal axis of the specimen. The corresponding masses 6 of each reciprocating mass means 1 are thereby reciprocated laterally in phase along a horizontal, lateral displacement path and a cyclic lateral load is applied to the specimen.

Further alternatively, and preferably, the above two configurations are combined to simultaneously apply cyclic bending and lateral loads to the specimen. In this configuration, two pairs of reciprocating mass means 1 are mounted on upper and lower surfaces and edges of the specimen, respectively. Simultaneously applying both cyclic bending and lateral loads to the specimen ensures the specimen is being realistically tested and the test conditions accurately simulate the conditions experienced by the specimen in service. For example, the specimen may be a wind turbine blade and the simultaneous application of cyclic bending and lateral loading to a blade realistically simulate the loads being applied to the blade by a prevailing wind whilst in service.

A reciprocating mass means 1 may be sized according to the size of specimen and, where the profile of the specimen permits, the base plate 2 of the reciprocating mass means 1 may mount direct to an outer surface of the specimen via bolt holes 18 and locating pins 20. However, where the specimen is substantially curved or has narrow edges, e.g. a wind turbine blade, for example, direct mounting of the base plate 2 to the specimen is difficult. In this case, it is particularly difficult to achieve a secure engagement of the base plate 2 of a reciprocating mass means 1 to a narrow edge of the specimen.

As shown in FIG. 2, an adjustable clamp 40 is used to mount one or more reciprocating mass means 1 to a specimen. The clamp 40 includes a platform 42 having a plurality of holes 44 each adapted to slideably receive a complementarily-shaped pin 46 having a first end 48 and a second end 50. The first end 48 of each pin 46 interfaces with an outer surface of the specimen. A resilient portion (not shown) may be disposed on the first end 48 of each pin 46 to protect the outer surface of the specimen when the clamp 40 is in situ. The resilient portion may be a cap placed over the first end 48 and may be a rubber material, for example.

The second end 50 of each pin 46 comprises a form of stop to limit the slideable movement of the pin 46 in the corresponding hole 44. The stop may be an outwardly extending shoulder, similar to a bolt head, or the pins 46 and holes 44 may be threaded, for example. Where the pins 46 and holes 44 are threaded, the clamp 40 is adjusted to a specimen profile by twisting each pin 46 in either a clockwise or anticlockwise direction to lower or raise the pin 46, respectively, in its corresponding hole 44. After adjustment, each pin 46 is constrained in its longitudinal direction by the screw threads. Of course, other means of adjusting and constraining the pins 46 may be used, such as an interference fit of each pin 46 within its corresponding hole 44, for example.

Advantageously, the clamp 40 is adjustable to allow the reciprocating mass means 1 to be mounted at any position along the specimen, particularly where the reciprocating mass means 1 is to be mounted on a substantially curved surface or narrow edge. The adjustable clamp 40 is also particularly convenient where the profile of the specimen, e.g. a wind turbine blade, is strictly confidential and a customer for whom the specimen is to be tested is reluctant to disclose the specimen profile before testing commences. With known systems, as described above, the profile must be supplied to the tester before testing commences to allow time for custom mounting brackets, for example, to be fabricated for the specific mounting position on the specimen. Where the profile of the specimen changes along its longitudinal axis and a different position for mounting the reciprocating mass means 1 is desired, e.g. a different loading point for a separate test, new mounting means must be fabricated specifically for the new position. By using an adjustable clamp 40, an advanced knowledge of the profile of the specimen at a desired location along the specimen is not required before testing, as might be the case for a bespoke clamping system, as the clamp 40 can simply be adjusted during setup of the apparatus before testing commences. Eliminating the need for custom-made mounting means reduces the time and cost required to set up the test.

The platform 42 of the clamp 40 has end plates 52, 54 to allow one or more clamps 40 to be joined in series for mounting to a large specimen, e.g. a wind turbine blade. One or more clamps 40 may be joined in series at their corresponding end plates 52 to provide a clamp set having a single platform. Two clamp sets can be connected in parallel to effectively clamp securely around the specimen.

As shown in FIG. 3, two clamp sets 60, 62 are mounted around the profile of a wind turbine blade 64, an upper clamp set 60 mounted on the upper surface of the blade 64 and a lower clamp set 62 mounted on the lower surface of the blade 64. One or more tie rods connect the two clamp sets together and securely clamp around the blade profile.

Each clamp set 60, 62 is adjusted to ensure its platform is horizontal and laterally orientated to the longitudinal axis of the blade 64. A single reciprocating mass means 68, 70 is centrally attached to the platform of each of the upper 60 and lower 62 clamps sets. The corresponding masses of the upper and lower reciprocating mass means 68, 70 are thereby reciprocated in phase with each other along their separate, parallel linear displacement paths by their corresponding actuators to apply a cyclic lateral load to the blade 64.

Alternatively, a single reciprocating mass means 72, 74 may be centrally attached to the outer end plates of the upper and lower clamp sets 60, 62 to provide two spaced reciprocating mass means 72, 74 on either side of the blade 64. The linear displacement paths of the side reciprocating mass means 72, 74 are separate and parallel and are vertically orientated. Therefore, the corresponding masses of the side reciprocating mass means 72, 74 are thereby reciprocated in phase with each other along their separate, parallel linear displacement paths by their corresponding actuators to apply a cyclic bending load to the blade 64.

As shown in FIG. 3, a more preferred embodiment is to attach a reciprocating mass means on the platforms of the upper and lower clamp sets 60, 62 and on the sides of the clamp sets 72, 74 thereby to provide an apparatus which is capable of simultaneously applying both cyclic bending and lateral loads to the blade 64. Providing a first pair of reciprocating mass means 60, 62 on the upper and lower surfaces of the blade 64 and a second pair of reciprocating mass means 72, 74 either side of the blade 64, ensures the bending and lateral loads applied to the blade 64 are balanced and the overall test configuration has minimal effects on the vibrational behaviour of the blade 64, particularly at its modes of resonance frequency.

The apparatus can operate in an 'open-loop' mode (i.e. without feedback) but it is preferred to provide the apparatus with a feedback loop to allow the apparatus to be operated in a 'closed-loop' mode. A feedback sensor may optionally be provided on the specimen to produce a feedback signal which is operatively associated with the control system. The feedback sensor may comprise a strain gauge, an accelerometer or a displacement sensor, for example. The control system is responsive to the feedback signal to operate each actuator of its corresponding reciprocating mass means in response to the feedback signal to change a displacement of its corresponding mass along its associated linear displacement path.

Where sensing of a displacement of the vibrating specimen is desired, a datum is mounted on, or otherwise defined on the surface of, the specimen and a datum tracking device, e.g. a camera, remotely positioned from the specimen tracks a position of the datum. The datum may be a point, line, edge or plane mounted on the specimen or a sticker or mark applied to the specimen. Alternatively, the datum may be a laser.

The invention claimed is:

1. An apparatus for applying at least one cyclical load to an elongate specimen, comprising:
    a first pair of reciprocating mass means each comprising a mass and an actuator, wherein the actuator is operatively associated with the mass to move the mass along a linear displacement path;
    the first pair of reciprocating mass means laterally spaced apart and mounted at opposing lateral sides of the elongated specimen whereby the linear displacement paths are oriented in a first direction and substantially parallel to one another; and
    a control system operatively associated with each actuator, the control system operating each actuator to reciprocate its corresponding mass along its respective linear displacement path to apply a cyclical load to the elongate specimen in the first direction.

2. An apparatus according to claim 1, further comprising a second pair of reciprocating mass means each comprising an actuator associated with a mass to move the mass along a linear displacement path, wherein the second pair of reciprocating mass means are mounted on opposing upper and lower surfaces of the elongated specimen whereby the linear displacement paths of the second pair of reciprocating mass means are oriented substantially parallel to one another and oriented in a second direction to simultaneously apply a cyclical load in the second direction substantially perpendicular to the first direction.

3. An apparatus according to claim 2, wherein the first direction is vertical relative to the upper and the lower surfaces to apply a bending load.

4. An apparatus according to claim 1, wherein the control system is adapted to move the corresponding masses of each reciprocating mass means along parallel displacement paths in phase with each other.

5. An apparatus according to claim 1, wherein the actuator is a linear hydraulic actuator.

6. An apparatus according to claim 1, comprising a feedback sensor operatively associated with said control system, the feedback sensor producing a feedback signal, said control system being responsive to the feedback signal thereby to operate each actuator in response to the feedback signal to change a displacement of each mass along its associated linear displacement path.

7. An apparatus according to claim 6, wherein the feedback sensor comprises a displacement sensor comprising a datum mounted on the elongate specimen and a camera remotely positioned from the elongate specimen which tracks a position of the datum.

8. An apparatus according to claim 7, wherein the datum comprises a laser.

9. An apparatus according to claim 1, wherein the first pair of reciprocating mass means are mounted to the elongate specimen by an adjustable clamp for clamping to an outer surface of the elongate specimen at any position along the elongate specimen.

10. An apparatus according to claim 1, wherein the reciprocating mass means are mounted to the elongate specimen by a clamp comprising a platform having a plurality of holes each slideably receiving a complementarily-shaped pin having a first end and a second end, wherein the first end of each pin interfaces with an outer surface of the elongate specimen.

11. An apparatus according to claim 10, wherein the second end of each pin comprises a stop to limit the slideable movement of the pin in the corresponding hole.

12. An apparatus according to claim 10, wherein the pins and holes are threaded.

13. A method for vibrating an elongate specimen, comprising:
    using reciprocating mass means each comprising a mass and an actuator operatively associated with its corresponding mass to move its mass along a linear displacement path;
    mounting a first pair of the reciprocating mass means in spaced relationship at lateral sides of the elongate specimen such that that the linear displacement paths are oriented in a first direction relative to an upper and a lower surface of the elongate specimen and substantially parallel to one another;
    reciprocating the masses of the first pair of the reciprocating mass means in the first direction; and
    applying a cyclical load to the elongate specimen in the first direction.

14. A method according to claim 13, comprising:
    mounting a secondary reciprocating mass means to the elongate specimen such that the associated linear displacement path is oriented in a second direction substantially perpendicular to the first direction; and
    reciprocating the mass of the secondary reciprocating mass means simultaneous with the reciprocating the masses of the first pair of the reciprocating means; and
    applying a cyclical load to the elongate specimen in the second direction.

15. A method according to claim 14, wherein the secondary reciprocating mass means comprises a secondary pair of the reciprocating mass means.

16. A method according to claim 14, wherein the first direction is along a vertical displacement path and the second direction is along a horizontal displacement path.

17. A method according to claim 13, comprising controlling the corresponding masses of each reciprocating mass means to move along parallel displacement paths in phase with each other.

18. A method according to claim 13, comprising:
    mounting a datum on the elongate specimen;
    positioning a camera remotely from the elongate specimen;
    tracking a position of the datum with the camera;
    detecting displacement of the elongate specimen; and
    controlling a displacement of the masses in accordance with the detection.

19. A method according to claim 18, wherein the datum comprises a laser.

20. A method according to claim 13, wherein the mounting the first pair of the reciprocating mass means comprises:
- an adjustable clamp comprising a platform having a plurality of holes each receiving a complementarily-shaped pin having a first end and a second end;
- adjusting each pin in accordance with a specimen profile so the first end of each pin interfaces with the surface of the specimen to mount the platform to the elongate specimen in a desired orientation; and
- attaching the pair of the reciprocating mass means to the platform.

21. An apparatus for applying a cyclical load to an elongate specimen, comprising:
- a first pair of reciprocating mass means each comprising a mass and an actuator, wherein the actuator is operatively associated with the mass to move the mass along a linear displacement path; and
- an adjustable clamp connectable to the elongate specimen at any position along a longitudinal axis of the elongate specimen to mount the first pair of reciprocating mass means on opposite sides of the elongate specimen such that the linear displacement paths of the pair of reciprocating mass means are oriented in a first direction and substantially parallel to one another, wherein the adjustable clamp comprises a platform having a plurality of holes each receiving a complementarily-shaped pin having a first end to interface with an outer surface of the elongate specimen and a second end.

22. The apparatus of claim 21, wherein the apparatus further comprises:
- a second pair of reciprocating mass means each comprising a mass and an actuator, wherein the actuator is operatively associated with the mass to move the mass along a linear displacement path, whereby the second pair of reciprocating mass means are connectable to the adjustable clamp for mounting in a spaced apart relation such that the linear displacement path of the second pair are oriented in a second direction substantially perpendicular to the first direction.

23. An apparatus according to claim 21, wherein each actuator is mounted at a first end to a base and at a second end to its corresponding mass.

24. An apparatus according to claim 23, wherein the mass is slideably mounted relative to the base.

25. An apparatus according to claim 21, wherein the second end of each pin comprises a stop to limit the slideable movement of the pin in the corresponding hole.

26. An apparatus according to claim 21, wherein the pins and holes are threaded.

* * * * *

UNITED STATES PATENT AND TRADEMARK OFFICE
CERTIFICATE OF CORRECTION

PATENT NO. : 8,505,387 B2
APPLICATION NO. : 12/937425
DATED : August 13, 2013
INVENTOR(S) : Waggot et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 320 days.

Signed and Sealed this
Fifteenth Day of September, 2015

Michelle K. Lee
*Director of the United States Patent and Trademark Office*